(12) United States Patent
Uchitel et al.

(10) Patent No.: US 10,130,599 B2
(45) Date of Patent: Nov. 20, 2018

(54) AGENT FOR PREVENTION AND TREATMENT OF OSTEOPOROSIS AND ITS USES

(71) Applicants: Mikhail Lvovich Uchitel, Mytishi (RU); Roman Anatolievich Trunin, Moscow (RU); Evgenij Iljich Maevskij, Pushino (RU)

(72) Inventors: Mikhail Lvovich Uchitel, Mytishi (RU); Roman Anatolievich Trunin, Moscow (RU); Evgenij Iljich Maevskij, Pushino (RU)

( * ) Notice: Subject to any disclaimer, the term of this patent is extended or adjusted under 35 U.S.C. 154(b) by 0 days.

(21) Appl. No.: 15/617,185

(22) Filed: Jun. 8, 2017

(65) Prior Publication Data

US 2018/0098953 A1 Apr. 12, 2018

(30) Foreign Application Priority Data

Oct. 11, 2016 (RU) .................................. 2016139956

(51) Int. Cl.
| | |
|---|---|
| *A61K 31/198* | (2006.01) |
| *A61K 33/06* | (2006.01) |
| *A61K 33/30* | (2006.01) |
| *A61K 31/593* | (2006.01) |
| *A61K 33/08* | (2006.01) |

(52) U.S. Cl.
CPC .......... *A61K 31/198* (2013.01); *A61K 31/593* (2013.01); *A61K 33/06* (2013.01); *A61K 33/08* (2013.01); *A61K 33/30* (2013.01)

(58) Field of Classification Search
CPC .... A61K 31/198; A61K 31/593; A61K 33/06; A61K 33/08; A61K 33/30
USPC .................................................. 514/1.1, 167
See application file for complete search history.

(56) References Cited

U.S. PATENT DOCUMENTS 9,216,184 B1 * 12/2015 Trunin ................. A61K 31/593
9,845,284 B1 * 12/2017 Uchitel ................. C07C 227/18

FOREIGN PATENT DOCUMENTS

RU 2220712 C1 * 1/2004

OTHER PUBLICATIONS

Costello et al, "The Important Role of Osteoblasts and Citrate Production in Bone Formation: "Osteoblast Citration" as a New Concept for an Old Relationship", 2012, The Open Bone Journal, 4, pp. 27-34. (Year: 2012).*

Rzymski et al., "The bioavailability of calcium in the form of pyruvate, carbonate, citrate-malate in healthy postmenopausal women", Jan. 2016, Eur Food Res Technol, 242(1), pp. 45-50. (Year: 2016).*

Grzesiak et al., "The Biological Role of α-Ketoglutaric Acid in Physiological Processes and Its Therapeutic Potential", Jan.-Mar. 2016, Dev. Period Med., 20(1), pp. 61-67. (Year: 2016).*

* cited by examiner

Primary Examiner — My-Chau T. Tran
(74) *Attorney, Agent, or Firm* — Bardmesser Law Group

(57) ABSTRACT

A mineral-vitamin complex for osteoporosis includes at least 92 mass % of the mineral-vitamin complex of amino acids and Krebs cycle acids and/or Krebs cycle acid salts, wherein the amino acids include glycine of between 1% and 80% of the mineral-vitamin complex, and wherein the Krebs cycle acids and/or Krebs cycle acid salts are up to 5 mass % of the mineral-vitamin complex; and valine, leucine and isoleucine such that a mass ratio of glycine to a sum of valine+leucine+isoleucine is in a range of 10-1000. Optionally, the valine, leucine and isoleucine are derived from dry milk, any stable dry product derived from milk and/or a mix thereof. Optionally, the following compounds are used as a source of Krebs cycle acid salts: Y-Me-Y.nH$_2$O, where Me—divalent metal, from Ca, Mg, Zn group, Y—anion of an acid participating in Krebs cycle, and n=0-12.

6 Claims, 3 Drawing Sheets

AGENT FOR PREVENTION AND TREATMENT OF OSTEOPOROSIS AND ITS USES

CROSS-REFERENCE TO RELATED APPLICATIONS

This application claims priority to RU 2016139956, filed on Oct. 11, 2016, which is incorporated by reference herein in its entirety.

BACKGROUND OF THE INVENTION

Field of the Invention

The invention relates to medicine and food manufacturing, and, more particularly, to a dietary supplement or over-the-counter medication for prevention and treatment of osteoporosis.

Description of the Related Art

Prevention and treatment of osteoporosis is an important health issue, since this disease currently afflicts about 20% of adults over the age of 60 and more than 45% of those who reach the age of 80. About 30% of femoral neck fractures are caused by osteoporosis.

There are several basic solutions to this problem. Mineral complexes in combination with vitamin D3 are the agents most widely used. The most popular is Calcemin Advance (manufactured by Bayer) [1], which contains: calcium (in the form of citrate and carbonate), magnesium (in the form of oxide), cholecalciferol (vitamin D3), copper and zinc (in their oxide forms), manganese sulfate and sodium borate. The main limitation of the known mineral complexes is that they are only effective as prophylactic agents and have no significant curative effect. In cases of already developed osteoporosis, administration of such mineral complexes without a complex therapy is useless.

Agents that are obtained from natural products with high calcium content are widely used. A product, for example, can be made as follows: crushed corrals or sea shells, or sea urchin skeletons, or egg shells or their combination are processed with organic acids or a mixture of several organic acids (such as acetic, gluconic, lactic, malic, fumaric, citric, amber or tartaric). These carbonates are processes thermally before or after reaction with organic acids at temperatures up to 700° C. with the subsequent purification of the product (see JPH 1014535, Jan. 20, 1998) [2]. Unfortunately, such products are also only prophylactic.

Known is a vitamin-mineral complex Absorbable Calcium plus Vitamin D3 made by Nature's Bounty [3] that contains soy lecithin and soy oil, in addition to calcium and vitamin D3. These products contain a significant amount of leucine; in mammals, leucine that comes from food which stimulates targets of rapamycin due to inhibition of adenosine monophosphate-activating protein kinase 1 and is thus able to activate signaling mechanism of rapamycin targets (mTOR), leading to the intensification of protein synthesis. Leucine simulation of the protein synthesis can achieve 30%. What is important is not the dose of leucine, but continuous delivery of leucine, for example, a month-long course, which is in line with an osteoporosis treatment strategy, see [4, 5, 6]. Based on the information from the manufacturer, this dietary supplement helps not only as a prophylactic agent, but is also capable of slowing down osteoporosis development, if the disease is already present.

Overall, all currently manufactured agents provide a source of calcium (and other necessary microelements) and, usually, their composition contains vitamin D3 to facilitate absorption and various other components to improve bone tissue health. All of this works well when there are no dysfunctions in the calcium absorption mechanisms which, in turn, are significantly tied to the signaling systems of the organism.

SUMMARY OF THE INVENTION

Accordingly, the present invention is related to an agent for prevention and treatment of osteoporosis that substantially obviates one or more of the disadvantages of the related art.

An exemplary mineral-vitamin complex for prevention and treatment of osteoporosis includes at least 92 mass % of the mineral-vitamin complex of amino acids and Krebs cycle acids and/or Krebs cycle acid salts, wherein the amino acids include glycine of between 1% and 80% of the mineral-vitamin complex, and wherein the Krebs cycle acids and/or Krebs cycle acid salts are up to 5 mass % of the mineral-vitamin complex; and valine, leucine and isoleucine such that a mass ratio of glycine to a sum of valine+leucine+isoleucine is in a range of 10-1000.

Optionally, the valine, leucine and isoleucine are derived from dry milk, any stable dry product derived from milk and/or a mix thereof. Optionally, the following compounds are used as a source of Krebs cycle acid salts:

$Y\text{-Me-}Y \cdot nH_2O$, where

Me—divalent metal, from Ca, Mg, Zn group,
Y—anion of an acid participating in Krebs cycle, and
n=0-12.

Optionally, the mineral-vitamin complex includes up to 10 mass % of any of vitamin D-group, vitamin B-group, vitamin C, vitamin E, vitamin F and/or a combination thereof. Optionally, the amino acids also include between 5 mass % and 86 mass % of acids selected from the group consisting of arginine, glutamic acid, tyrosine, taurine, aspartic acids, serine, D-serine, carnitine and/or their pharmaceutically acceptable salts. Optionally, the composition is in a form tablets, capsules, dragée, powder, pastilles, suspension, or a solution. Optionally, sugar and/or sweeteners and/or microcrystalline cellulose and/or technological additive and ballast products are added to the complex.

Additional features and advantages of the invention will be set forth in the description that follows, and in part will be apparent from the description, or may be learned by practice of the invention. The advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE ATTACHED FIGURES

The accompanying drawings, which are included to provide a further understanding of the invention and are incorporated in and constitute a part of this specification, illustrate embodiments of the invention and together with the description serve to explain the principles of the invention.

DETAILED DESCRIPTION OF THE PREFERRED EMBODIMENTS

Figure 1:
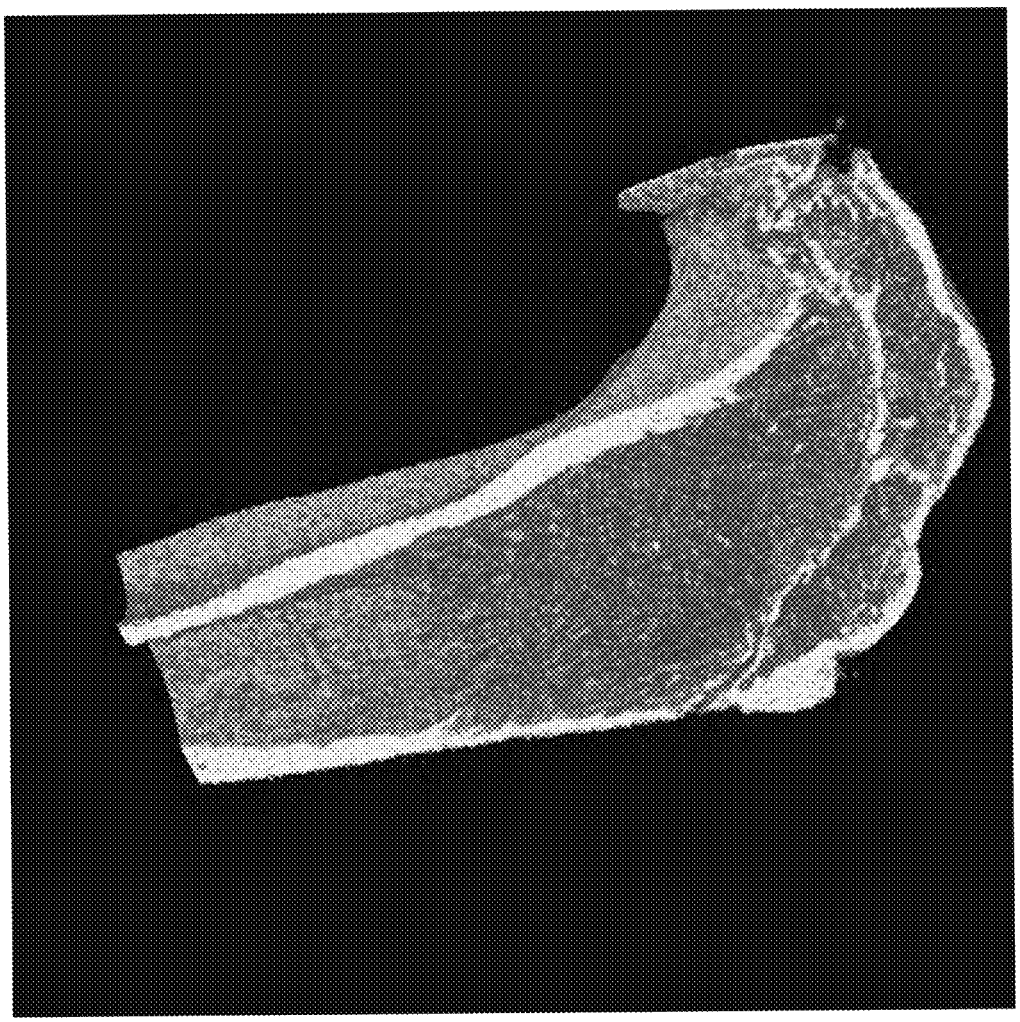
FIG. 1 shows an example of a 3D model of a shin bone fragment from group CII (negative control) with the signs of involutional osteoporosis.

Reference will now be made in detail to the preferred embodiments of the present invention.

The solution provided by this invention is aimed at the restoration of normal bone tissue synthesis, thus providing a real therapeutic effect. The restoration of normal bone tissue synthesis is only possible when 3 conditions are met: first, the organism must be provided with an easy source of calcium, second—the organism must be provided with components that support synthesis of bone tissue and collagen (vitamins, microelements, amino acids, Krebs cycle substrates), third—with restoration of regulatory and signaling systems.

The problem is solved by ensuring that the supplement, besides sources of calcium, microelements, vitamins and others, also contains components that provide improvements of body's regulatory function, specifically—glycine and the 3 amino acids—valine, leucine, isoleucine (tri-part complex of branched chain amino acids). These amino acids play a regulatory role in protein biosynthesis. First, leucine, isoleucine and valine suppress secretion of the stress hormone cortisol and the corresponding pituitary tropic hormone. As a result, there is an increase in synthesis of androgens that have a pronounced anabolic effect. In other words, branched chain amino acids allow, despite stress conditions, for the support of protein biosynthesis, specifically collagen, thanks to their regulatory anabolic effect.

With advanced age, when the physical load on the organism is much lower, and development of involutional osteoporosis takes place, the need for the support of collagen synthesis (collagen has slow turnover and is renewed during a period of over 300 days) takes first place. In this situation, the use of high doses of branched chain amino acids does not make sense, since such amounts cannot be utilized in collagen biosynthesis and will simply be transitory, while unnecessarily putting stress on the transport systems of the mucous membrane cells of the GI tract, liver and excretory kidney system. Therefore, the above-mentioned amino acids are required in small doses if needed, but for a long time—providing prevention and treatment of osteoporosis.

Taking glycine, which is especially effective before sleep, causes a significant increase in the blood levels of the growth hormone—the main anabolic hormone. Non-sugar-bound glycine, arginine, tyrosine and ornithine are the main initiators of the growth hormone release from the pituitary that occurs during age-related weakening of the gland's function. Here we once again encounter the synergetic anabolic effect of glycine and the above-mentioned anabolic effect of leucine, isoleucine and valine. Glycine also acts as the most important neurotransmitter, that allows, for example, for the normalization of functionally important relationships of metabotropic receptros activities of γ-aminobutyric, γ-hydroxybutyric and glutamic acids.

The inventors have concluded that using glycine in substrate doses (roughly $10^{-3}$ mol/liter, compared to signaling doses, which are roughly 2 orders of magnitude smaller) in vitamin-mineral complexes in combination with the 3 amino acids—valine, leucine, isoleucine (mass ratio of glycine to the sum of leucine+isoleucine+valine=10-1000) results in restoration of active bone tissue synthesis, even under conditions of developing osteoporosis. In the sum of leucine+isoleucine+valine, each of the amino acids should be at least 2% of the total. Dry milk or any other stable dry product derived from milk and/or mix of such products can be used as a source of valine, leucine and isoleucine. For a source of divalent microelements, we propose to use at least one of the compounds of the following formula:

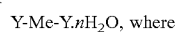

Y-Me-Y.$n$H$_2$O, where

Me—divalent metal, from Ca, Mg, Zn group

Y—anion of an acid participating in Krebs cycle (e.g., fumaric acid, citric acid, isocitric acid, alphaketaglutarate, succinic acid, malic acid)

n=0-12.

Vitamins from groups D, B, C, E, F and/or their combination are used as sources of vitamins Additionally, we recommend using amino acids from: arginine, glutamic acid, tyrosine, taurine, aspartic acid, serine, D-serine, carnitine and/or their pharmaceutically acceptable salts.

The agent is proposed to be manufactured in form of tablets, capsules, dragée, powder or pastilles. Additionally, the agent can include sugar and/or sweeteners and/or microcrystalline cellulose and/or technological additive and ballast products.

Prophylactic and therapeutic effects are achieved by taking the agent in long courses (several months or years) or continuously for the rest of the patient's life.

The possibilities of industrial use of the proposed invention are illustrated below with the following examples.

Example 1

Vitamin D3 is added to calcium gluconate. BCAA (Branched Chain Amino Acid) is added to glycine. The two resulting mixes are then combined together and calcium citrate is added, resulting in the following composition (in this example and other examples below, the listed mass percentage values should be treated as ±7%, more preferably ±5%):

Calcium gluconate—80 mass %
Calcium citrate—14.9485 mass %
Vitamin D3—0.0015 mass %
Glycine—5 mass %
BCAA—0.05 mass %

Example 2

Vitamin D3 is added to calcium chloride. BCAA is added to magnesium oxide. The two resulting mixes are combined together, followed by addition of glycine and calcium isocitrate, resulting in the following composition:

Calcium isocitrate—8 mass %
Calcium chloride—75 mass %
Magnesium oxide—9.999 mass %
Vitamin D3—0.001 mass %
Glycine—2 mass %
Milk powder (source of BCAA)—5 mass % (0.04 mass % BCAA).

Example 3

Vitamin D3 is added to calcium chloride. BCAA is added to glycine. The two resulting mixes are combined together, followed by addition of vitamin E (in silicate carrier), zinc chloride and calcium malate acidic tetrahydrate, resulting in the following composition:
- Calcium malate acidic tetrahydrate—20 mass %
- Calcium chloride—55 mass %
- Zinc chloride—7 mass %
- Vitamin D3—0.003 mass %
- Glycine—15 mass %
- BCAA—0.035 mass %
- Vitamin E—2.962 mass %

Example 4

Vitamin D3 is added to calcium succinate (acidic), and then Vitamin E is added. The resulting mixture is then combined with magnesium succinate (acidic tetrahydrate), zinc fumarate (acidic hydrate), sodium monoglutamate (monohydrate), glycine, and dry milk. The result is the following composition:
- Calcium succinate, acidic—40 mass %
- Magnesium succinate, acidic tetrahydrate—8 mass %
- Zinc fumarate, acidic hydrate—3 mass %
- Vitamin E—2 mass %
- Vitamin D3—0.001 mass %
- Sodium monoglutamate, monohydrate—4.999 mass %
- Glycine—9 mass %
- Dry milk (source of BCAA)—33 mass % (0.25 mass % BCAA)

Example 5

The prepared mixes based on examples 1-4 can then be used to obtain commercial product in various forms and by various methods. Below are different technological options for obtaining partially prepared products and the final product.

Obtaining mixtures with specified portions by dosing directly from the resulting combinations, or the granules can be prepared from the resulting mix as follows: 2 parts of the mix are combined with one dose of glucose and one dose of casein; the resulting mix is moistened to the point of viscous flow; granules weighing 0.50 g are then obtained via a dispenser with air flow parallel to the mirror dispenser.

Alternatively, tablets with specific weight can be obtained from the resulting mix directly via dry pressing. Alternatively, tablets with specific weight can be obtained by adding one part of corn starch and one part lactose to two parts of the mix and then using direct dry pressing. Alternatively, gelatin capsules of required size can be filled directly from the prepared mix. Alternatively, a suspension with 10% of the agent can be obtained by suspending one part of the mix in 9 mass parts of refined sterilized olive oil. Alternatively, 20% mix of the solution and suspension can be obtained by suspending one part of the mixture in 4 mass parts of distilled water.

Example 6

Evaluation of prophylactic properties of the agents were conducted based on the methods developed by the Russian Institute of Space Studies in order to evaluate development and study the possibility of reversing osteoporosis under conditions of prolonged weightlessness in a space station. Using elastic tape, male rats were suspended by tail (hind paws did not touch the floor of the cage). After 7 day of acclimation, the animals received 3 g of cottage cheese in addition to standard diet for 7 days. Then for 14 days, the agent being tested was added to cottage cheese (40 mg per kg of animal weight). The animals were then sacrificed; tibia and fibula of hind legs were obtained and were subjected to X-ray densitometry.

Wistar line rats (3 months old) were divided into the following groups:

1. Group 1—Control I (C I)—Intact Animals.

12 males (average weight—315.5±10.0 g) were fed standard vivarium diet (dry food "Normokorm", sufficient amount of drinks) and kept 6 animals per cage.

2. Group 2—Control II (C II).

10 males (average weight—313.4±8.8 g) were suspended by their tail; (hind paws could not reach the floor of the cage); after 7 days of acclimation, the animals were fed, in addition to regular diet, 3 g of cottage cheese (placebo) for 21 days. Each animal was kept in an individual cage.

3. Group 3—Experiment with Absorbable Calcium plus Vitamin D3.

12 males (average weight—308±6.5 g.) were suspended by their tail; (hind paws could not reach the floor of the cage); after 7 days of acclimation, the animals were fed, in addition to regular diet, 3 g of cottage cheese for 7 days and then cottage cheese with the indicated supplement (60 mg kg of animal weight) for 14 days.

4. Group 4—Experiment with the Supplement from Example 1.

12 males (average weight—317±8.9 g) were suspended by their tail; (hind paws could not reach the floor of the cage); after 7 days of acclimation, the animals were fed, in addition to regular diet, 3 g of cottage cheese for 7 days and then cottage cheese with the indicated supplement (40 mg kg of animal weight) for 14 days.

5. Group 5—Experiment with the Supplement from Example 2.

12 males (average weight—301±4.2 g) were suspended by their tail; (hind paws could not reach the floor of the cage); after 7 days of acclimation, the animals were fed, in addition to regular diet, 3 g of cottage cheese for 7 days and then cottage cheese with the indicated supplement (40 mg kg of animal weight) for 14 days.

6. Group 6—Experiment with the Supplement from Example 3.

12 males (average weight—311±4.5 g) were suspended by their tail; (hind paws could not reach the floor of the cage); after 7 days of acclimation, the animals were fed, in addition to regular diet, 3 g of cottage cheese for 7 days and then cottage cheese with the indicated supplement (40 mg kg of animal weight) for 14 days.

7. Group 7—Experiment with the Supplement from Example 4.

12 males (average weight—297.6±4.8 g) were suspended by their tail; (hind paws could not reach the floor of the cage); after 7 days of acclimation, the animals were fed, in addition to regular diet, 3 g of cottage cheese for 7 days and then cottage cheese with the indicated supplement (40 mg kg of animal weight) for 14 days.

The animals were then sacrificed and shin bones of the hind legs were isolated. The bones were subjected to X-ray densitometry. Measurements were done with Lunar Prodigj Ge Advance with the following settings: voltage—76 Rv; current—0.15 mA; time 1 min 7 sec; dose 2/0 mGr.

TABLE 1

Shin bone density based on X-ray densitometry.

| | Group | Bone density (shin), g/cm$^3$ | Bone preservation compared to control I, % | Bone preservation compared to control II, % |
|---|---|---|---|---|
| 1. | Control I | 0.146 ± 0.011 | 100 | |
| 2. | Control II | 0.128 ± 0.009 | 87.7 | |
| 3. | Experiment with the closet analogue | 0.134 ± 0.076 | 91.8 | 104.7 |
| 4. | Experiment based on example 1 | 0.136 ± 0.077 | 93.2 | 106.25 |
| 5. | Experiment based on example 2 | 0.139 ± 0.093 | 95.2 | 108.6 |
| 6. | Experiment based on example 3 | 0.139 ± 0.059 | 95.2 | 108.6 |
| 7. | Experiment based on example 4 | 0.142 ± 0.043 | 97.3 | 110.9 |

All the supplements demonstrated positive dynamics relative to the negative control C II (developed osteoporosis). However, supplements prepared as in examples 1-4 demonstrated higher effectiveness. The results allow to view the actions of these supplements as therapeutic, especially for the one in example 4.

Example 7

The therapeutic action of the supplements was investigated in older animals. The experiments were conducted as follows: female rats (Sprague Dawley line) undergone unilateral ovariectomy at 10 months of age; the animals (except for those in Control I group) were each kept in separate long, tall (25×25 cm) and very narrow cages (about 8 cm). The animals were 18 months old at the beginning of the experiment. The experiment lasted 1 month.

The animals were divided into 7 groups:

Group 1—control I. 12 rats, intact animals (starting weight 504-649 g, ending weight 511-667 g) were fed standard vivarium diet (dry food "Normokorm", unlimited drinks).

Group 2—control II (negative control). 12 animals (starting weight 512-670 g; ending weight 519-658 g) were fed standard vivarium diet (dry food "Normokorm", unlimited drinks) plus 3 g of cottage cheese.

Group 3—experiment with Absorbable Calcium plus Vitamin D3. 12 rats (starting weight 534-612 g; ending weight 505-623) were fed standard vivarium diet (dry food "Normokorm", unlimited drinks) plus daily 3 g of cottage cheese to which indicated supplement was added (60 mg per kg of animal weight).

Group 4—experiment with the supplement from example 1. 12 rats (starting weight 552-597 g; ending weight 525-611) were fed standard vivarium diet (dry food "Normokorm", unlimited drinks) plus daily 3 g of cottage cheese to which the supplement from example 1 was added (40 mg per kg of animal weight).

Group 5—experiment with the supplement from example 2. 12 rats (starting weight 558-621 g; ending weight 531-642 g) were fed standard vivarium diet (dry food "Normokorm", unlimited drinks) plus daily 3 g of cottage cheese to which the supplement from example 2 was added (40 mg per kg of animal weight).

Group 6—experiment with the supplement from example 3. 12 rats (starting weight 539-616 g; ending weight 541-637 g) were fed standard vivarium diet (dry food "Normokorm", unlimited drinks) plus daily 3 g of cottage cheese to which the supplement from example 3 was added (40 mg per kg of animal weight).

Group 7—experiment with the supplement from example 4. 12 rats (starting weight 549-634 g; ending weight 532-638 g) were fed standard vivarium diet (dry food "Normokorm", unlimited drinks) plus daily 3 g of cottage cheese to which the supplement from example 4 was added (40 mg per kg of animal weight).

Prior to the experiments, the animals were fed cottage cheese for 3 days. Cottages cheese balls (placebo and with added supplements) were given individually to each animal in the first half of the day (10-11 am) for 1 month, including Saturdays and Sundays.

The animals were scarified by decapitation after a light ether anesthesia. Hind legs were obtained and studied in two stages. At the first stage, a 3D model of each shin bone was created using X-ray tomography, Bruker Skyscan 1176 (Bruker, 2012).

The invention is illustrated with the following figures:

FIG. 1. Example of a 3D model of a shin bone fragment from group CII (negative control) with the signs of involutional osteoporosis.

Figure 2:
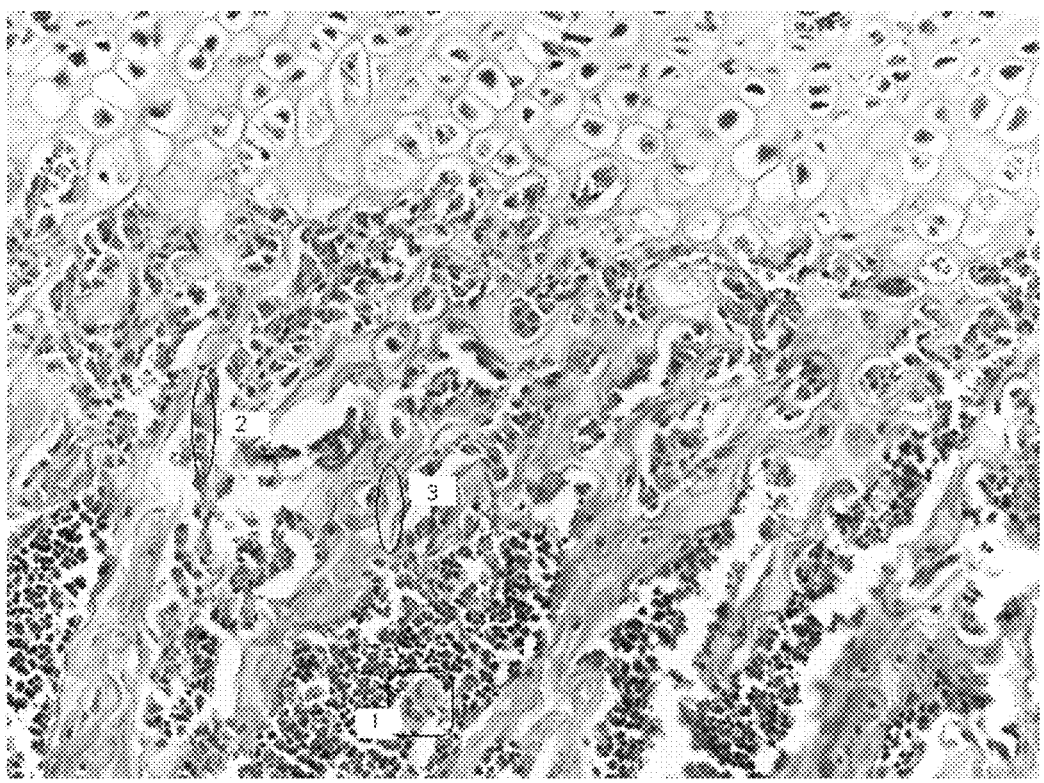
FIG. 2 shows front leg bone metaphysis area, control animal.

FIG. 2. Front leg bone metaphysis area, control animal.

Figure 3:
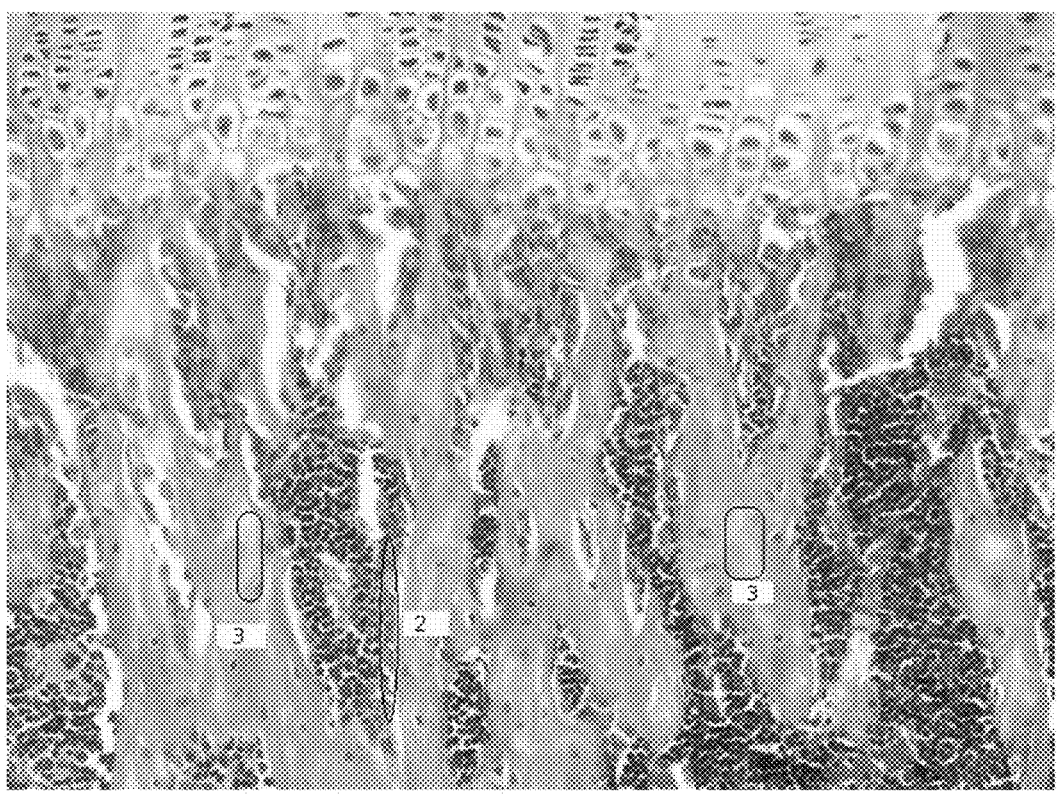
FIG. 3 shows metaphysis of the front leg of an animal with osteoporosis after administration of the supplement from example 4.

FIG. 3. Metaphysis of the front leg of an animal with osteoporosis after administration of the supplement from example 4.

Since studying the entire femur is time-consuming and, more importantly, not very informative, we investigated metabolically active metaphysis and adjacent areas—the tubular part (near the hip joint) part of femur. This is where osteoporosis actively develops, but two pathological processes do not here occur at the same time: osteoporosis and changes in the cartilage of the joint, which add a layer of additional changes. Closer to the middle, the bone changes from spongy to tubular and osteoporosis occurs there only at the last stage of bone destruction.

3D imaging of the obtained bone fragment with soft tissue was conducted. Based on the contract/density ratio, soft tissues were subtracted in the 3D model; the final model was then created, where density can be calculated at any point. The animals' legs were not subject to any mechanical manipulation.

All animals (except the healthy animals in the control I group) were diagnosed with osteoporosis based on the results of X-ray tomography.

The parameters that are directly affected by presence/absence of osteoporosis were calculated. First, bone surface/volume ratio, S/V, mm—ratio of the surface area of the bone to the enclosed volume of bone tissue in it. Second, trabecular thickness, TTh, mm Primary damage of the bone tissue due to osteoporosis is first reflected in the decrease of trabecular thickness. The thicker the trabecula, the higher bone mechanical properties.

Calculations were done using Statistica 12 [7].

Since all collected data turned out to be non-Gaussian (i.e. having non-normal distribution), non-parametric calculation methods have been applied.

The results are provided below:

TABLE 2

T-test, comparison of C II to C I groups

| Parameter | Mean C II | Mean C I | p | Valid N CII | Valid N CI |
|---|---|---|---|---|---|
| S/V | 38.7439 | 34.1984 | 0.00015 | 28 | 28 |
| TTh | 0.08779 | 0.12158 | 0.00068 | 28 | 28 |

TABLE 3

T-test, comparison of the analogous group (Group 3) to C II and C I

| Parameter | Group 3 mean | Mean C I | p | Valid N Group 3 | Valid N CI |
|---|---|---|---|---|---|
| S/V | 38.2151 | 34.1984 | 0.00114 | 28 | 28 |
| TTh | 0.08932 | 0.12158 | 0.00143 | 28 | 28 |

| Parameter | Group 3 mean | Mean C II | p | Valid N Group 3 | Valid N CI |
|---|---|---|---|---|---|
| S/V | 38.2151 | 38.7439 | 0.17175 | 28 | 28 |
| TTh | 0.08932 | 0.08779 | 0.62818 | 28 | 28 |

TABLE 4

T-test, comparison of Group 4 (supplement from example 1) to C II and C I

| Parameter | Mean group 4 | Mean C I | p | Valid N Group 4 | Valid N KI |
|---|---|---|---|---|---|
| S/V | 36.9812 | 34.1984 | 0.00197 | 28 | 28 |
| TTh | 0.09791 | 0.12158 | 0.00218 | 28 | 28 |

| Parameter | Mean Group 4 | Mean C II | p | Valid N Group 4 | Valid N KI |
|---|---|---|---|---|---|
| S/V | 36.9812 | 38.7439 | 0.00119 | 28 | 28 |
| TTh | 0.09791 | 0.08779 | 0.00157 | 28 | 28 |

TABLE 5

T-test, comparison of Group 5 (supplement from example 2) to C II and C I

| Parameter | Group 5 mean | Mean C I | p | Valid N Group 5 | Valid N CI |
|---|---|---|---|---|---|
| S/V | 37.2297 | 34.1984 | 0.00175 | 28 | 28 |
| TTh | 0.10067 | 0.12158 | 0.00249 | 28 | 28 |

| Parameter | Group 5 mean | Mean C II | p | Valid N Group 5 | Valid N CI |
|---|---|---|---|---|---|
| S/V | 37.2297 | 38.7439 | 0.00227 | 28 | 28 |
| TTh | 0.10067 | 0.08779 | 0.00197 | 28 | 28 |

TABLE 6

T-test, comparison of Group 6 (supplement from example 3) to C II and C I

| Parameter | Group 6 mean | Mean C I | p | Valid N Group 6 | Valid N CI |
|---|---|---|---|---|---|
| S/V | 36.1287 | 34.1984 | 0.00141 | 28 | 28 |
| TTh | 0.11006 | 0.12158 | 0.00188 | 28 | 28 |

| Parameter | Group 6 mean | Mean C II | p | Valid N Group 6 | Valid N CI |
|---|---|---|---|---|---|
| S/V | 36.1287 | 38.7439 | 0.00134 | 28 | 28 |
| TTh | 0.11006 | 0.08779 | 0.00099 | 28 | 28 |

TABLE 7

T-test, comparison of Group 7 (supplement from example 4) to C II and C I

| Parameter | Group 7 mean | Mean C I | p | Valid N Group 7 | Valid N CI |
|---|---|---|---|---|---|
| S/V | 35.5206 | 34.1984 | 0.00127 | 28 | 28 |
| TTh | 0.11718 | 0.12158 | 0.00105 | 28 | 28 |

| Parameter | Group 7 mean | Mean C II | p | Valid N Group 7 | Valid N CI |
|---|---|---|---|---|---|
| S/V | 35.5206 | 38.7439 | 0.00112 | 28 | 28 |
| TTh | 0.11718 | 0.08779 | 0.00087 | 28 | 28 |

As can be seen from Tables 2-7, animals from groups CII and Groups 3-7 have developed osteoporosis. From table 3, we can see that complex Absorbable Calcium plus Vitamin D3 does not treat the disease. In groups 4-7, the development of osteoporosis is partially compensated. Especially effective was the supplement prepared as in example 4.

Example 8

After X-ray tomography, animals' hind legs were subject to histological evaluations. Histology was conducted on the shin bones of the right hind legs on 6 animals from each group. Complete study is extremely difficult because of the high volume of the work.

Prior to the analysis, cells of the bone tissue in intact healthy animals (Control I) were marked.

FIG. 2 shows: osteoclast 1, osteoblast 2, area 3 of transition state from chondrocytes into osteoid cells stained with light pink color. The staining is done with hematoxylin-eosin. Magnification 10×20.

Based on the obtained basal markers, further evaluation of the material was conducted.

FIG. 3 shows: osteoblast 2, area 3 of transitional state from chondrocytes to osteoid cells stained with light pink color. The staining is done with hematoxylin-eosin. Magnification 10×20.

The number of osteoblasts and osteoclasts were calculated in the viewing field for each section.

After that, the % changes of their ratio compared to group CI was determined. The results are presented in Table 8.

TABLE 8

Ratio of osteoblasts to osteoclasts in the shin bone of right hind leg.

| Group | Number of bones | Changes relative to CI, % | p |
|---|---|---|---|
| Control II | 6 | −89.4 | <0.01 |
| Group 3 | 6 | −87.7 | <0.05 |
| Group 4 | 6 | −33.6 | <0.01 |

TABLE 8-continued

Ratio of osteoblasts to osteoclasts in the shin bone of right hind leg.

| Group | Number of bones | Changes relative to CI, % | p |
|---|---|---|---|
| Group 5 | 6 | −28.4 | <0.01 |
| Group 6 | 6 | −9.5 | <0.01 |
| Group 7 | 6 | +5.6 | <0.01 |

As can be seeing from Table 8, supplements from examples 1-4 allow to support function of osteoblasts, which in turn provides therapeutic anti-osteoporosis effect.

After sacrifice, the animals in the examples 6 and 7 were subject to patho-morphological analysis of the main organs. No morphological signs of pathological osteogenesis, degenerative or inflammatory processes caused by prolonged intake of the supplements were observed. No counter-indications was determined. This allows for the use of proposed supplements in prolonged or chronic treatment courses.

Having thus described a preferred embodiment, it should be apparent to those skilled in the art that certain advantages of the described composition have been achieved.

It should also be appreciated that various modifications, adaptations, and alternative embodiments thereof may be made within the scope and spirit of the present invention. The invention is further defined by the following claims.

REFERENCES

[1]—www.bayer.com/
[2]—Patent JPH1014535, 20 Jan. 1998
[3]—www.naturesbounty.com/
[4]—M. Du, Q. W. Shen, M. J. Zhu, S. P. Ford, Leucine stimulates mammalian target of rapamycin signaling in $C_2C_{12}$ myoblasts in part through inhibition of adenosine monophosphate-activated protein kinase1//J. Animal Science. 2014
[5]—Anthony, J. C., T. G. Anthony, S. R. Kimball, and L. S. Jefferson. 2001. Signaling pathways involved in translational control of protein synthesis in skeletal muscle by leucine. J. Nutr. 131:856S-860S
[6]—Martin, D. E., and M. N. Hall. 2005 The expanding TOR signaling network. Curr. Opin. Cell Biol. 17:158-166
[7]—www.statsoft.com/Products/STATISTICA-Features/version-12

What is claimed is:

1. A compound for prevention and treatment of osteoporosis, comprising:
a mineral-vitamin complex, wherein the mineral-vitamin complex is up to 92 mass % of the compound,
wherein the mineral-vitamin complex includes fumaric, succinic and/or malic acids, and/or salts of Ca, Mg and/or Zinc derived from Y-Me-Y.$nH_2O$, where
Me is Ca, Mg or Zn,
Y is an anion of fumaric, succinic and malic acids, and n=0-12,
wherein the vitamins are up to 5 mass % the mineral-vitamin complex include any of vitamin D-group, vitamin B-group, vitamin E, and/or a combination thereof,
wherein the amino acids include glycine between 1 mass % and 80 mass % of the mineral-vitamin complex,
wherein the amino acids also include between 5 mass % and 86 mass % of the mineral-vitamin complex of glutamic acid, sodium glutamate and/or aspartic acids; and
valine, leucine and isoleucine such that a mass ratio of glycine to a sum of valine+leucine+isoleucine is in a range of 10-1000, and is no more than 8 mass % of the compound.

2. The mineral-vitamin complex of claim 1, the valine, leucine and isoleucine are derived from dry milk, any stable dry product derived from milk and/or a mix thereof.

3. The mineral-vitamin complex of claim 1, wherein the composition is in a form tablets, capsules, dragée, powder, pastilles, suspension, or a solution.

4. The mineral-vitamin complex of claim 3, further comprising sugar and/or sweeteners and/or microcrystalline cellulose and/or technological additive and ballast products.

5. A method of prevention and treatment of osteoporosis, comprising providing, to a patient a compound that comprises:
a mineral-vitamin complex, wherein the mineral-vitamin complex is up to 92 mass % of the compound,
wherein the mineral-vitamin complex includes fumaric, succinic and/or malic acids, and/or salts of Ca, Mg and/or Zinc derived from Y-Me-Y.$nH_2O$, where
Me is Ca, Mg or Zn,
Y is an anion of fumaric, succinic and malic acids, and n=0-12,
wherein the vitamins are up to 5 mass % the mineral-vitamin complex include any of vitamin D-group, vitamin B-group, vitamin E, and/or a combination thereof,
wherein the amino acids include glycine between 1 mass % and 80 mass % of the mineral-vitamin complex,
wherein the amino acids also include between 5 mass % and 86 mass % of the mineral-vitamin complex of glutamic acid, sodium glutamate and/or aspartic acids; and
valine, leucine and isoleucine such that a mass ratio of glycine to a sum of valine+leucine+isoleucine is in a range of 10-1000, and is no more than 8 mass % of the compound.

6. The method of claim 5, wherein a delivery of the composition is a long course of treatment or a continuous delivery.

\* \* \* \* \*